US007064111B1

(12) United States Patent
Todo et al.

(10) Patent No.: US 7,064,111 B1
(45) Date of Patent: Jun. 20, 2006

(54) USE OF SOLUBLE COSTIMULATORY FACTOR FOR TUMOR IMMUNO-GENE THERAPY

(75) Inventors: Tomoki Todo, Belmont, MA (US); Samuel D. Rabkin, Lynn, MA (US); Robert L. Martuza, Cambridge, MA (US)

(73) Assignee: Georgetown University, Washington, DC (US)

( * ) Notice: Subject to any disclaimer, the term of this patent is extended or adjusted under 35 U.S.C. 154(b) by 17 days.

(21) Appl. No.: 09/679,147

(22) Filed: Oct. 5, 2000

Related U.S. Application Data (60) Provisional application No. 60/157,787, filed on Oct. 5, 1999.

(51) Int. Cl.
| | |
|---|---|
| A61K 48/00 | (2006.01) |
| A61K 39/12 | (2006.01) |
| A61K 39/245 | (2006.01) |
| C12N 15/00 | (2006.01) |
| C12N 5/00 | (2006.01) |

(52) U.S. Cl. ............... 514/44; 435/320.1; 435/325; 435/455; 424/199.1; 424/231.1; 424/134.1

(58) Field of Classification Search ............. 435/320.1, 435/325; 514/44
See application file for complete search history.

(56) References Cited

U.S. PATENT DOCUMENTS

| | | | | |
|---|---|---|---|---|
| 6,051,428 A | * | 4/2000 | Fong et al. | 435/456 |
| 6,310,045 B1 | * | 10/2001 | Barber et al. | 514/44 |
| 6,764,675 B1 | * | 7/2004 | Whitley et al. | 424/93.2 |

OTHER PUBLICATIONS

Verma et.al.; Gene therapy-promises, problems and prospects, 1997, Nature, vol. 389: 239-242.*
Miller et.al.; Targeted vectors for gene therapy, 1995, FASEB J. 9; 190-199.*
Marshall; Gene Therapy's Growing Pains, 1995, Science, vol. 269: 1050-1055.*
Orkins et.al; Report and Recommendations of the Panel to Assess the NIH Ivestment in Research on Gene Therapy, 1995.*
Deonarain; Ligand-targeted receptor-mediated vectors for gene delivery, 1998, Exp. Opin. Ther. Patents 8(1): 53-69.*
Restifo et.al.; Molecular Mechanisms Used by Tumors to Escape Immune Recognition: Immunogenetherapy and the Cell Biology of Major Histocompatibility Complex Class I: 1993, Journal of Immunotherapy 14: 182-190.*
Sturmhoefel et.al.; Potent Activity of Soluble B7-IgG Fusion Proteins in Therapy of Established Tumors and as Vaccine Adjuvant, 1999, Cancer Research59: 4964-4972.*

Hollenbaugh et.al.; The human T cell antigen gp39, a member of the TNF gene family, is a ligand for the CD40 receptor: expression of a soluble form gp39 with B cell co-stimulatory activity, 1992, The EMBRO Journal, vol. 11, No. 12: 4313-4321.*
M. Albert, et al. "Dendritic cells acquire antigen from apoptotic cells and induce class 1-restricted CTLs", The Rocekfeller University, New York, NY, *Letters to Nature*, 392: 86-89 (1998).
S. Baskar, et al. "Rejection of MHC Class II-Transfected Tumor Cells Requires Induction of Tumor-Encoded B7-1 and/or B7-2 Costimulatory Molecules", The American Association of Immunologists, Bethesda, MD, *The Journal of Immunology*, 156: 3821-3827 (1996).
F. Cavallo, et al. "Co-expression of B7-1 and ICAM-1 on tumors is required for rejection and the establishment of a memory response", VCH Publishers, Inc. Deerfield Beach, FL, *European Journal of Immunology*, 25: 1154-1162 (1995).
P. Chaux, et al. "Inflammatory Cells Infiltrating Human Colorectal Carcinomas Express HLA Class II but Not B7-1 and B7-2 Costimulatory Molecules of the T-Cell Activation", United States and Canadian Academy of Pathology, Inc., USA, *Laboratory Investigation*, 74: 975-983 (1996).
L. Chen, et al. "Tumor Immunogenicity Determines the Effect of B7 Costimulation on T Cell-mediated Tumor Immunity", The Rockefeller University Press, New York, NY, *Journal of Experimental Medicine*, 179: 523-532 (1994).
R. Denfeld, et al. "*In Situ* Expression of B7 and CD28 Receptor Families in Human Malignant Melanoma: Relevance for T-Cell-Mediated Anti-Tumor Immunity", Wiley-Liss, Inc., New York, NY, *International Journal of Cancer*, 62: 259-265 (1995).
F. Falkner, et al. "*Escherichia coli gpt* Gene Provides Dominant Selection for Vaccina Virus Open Reading Frame Expression Vectors", American Society for Microbiology, Washington, DC, *Journal of Virology*, 62: 1849-1854 (1988).
F. Falkner, et al. "Transient Dominant Selection of Recombinant Vaccina Viruses", American Society for Microbiology, Washington, DC, *Journal of Virology*, 64: 3108-3111 (1990).
J. Galea-Lauri, et al. "Novel costimulators in the immune gene therapy of cancer", Nature Publishing Group, New York, NY, *Cancer Gene Therapy*, 3:202-214 (1996).

(Continued)

*Primary Examiner*—Anne M. Wehbe'
(74) *Attorney, Agent, or Firm*—Foley & Lardner LLP (57) ABSTRACT

A new gene therapy entails tumor treatment by introducing an expressible nucleotide sequence for a soluble costimulatory factor, thereby enhancing the response of T-cells to a tumor. In vivo expression of the soluble factor overcomes anergy or tolerance to tumor cells and activates T-cells that are infiltrating or surrounding the tumor. A pharmaceutical composition containing such a gene is effective in tumor suppression.

16 Claims, 4 Drawing Sheets

OTHER PUBLICATIONS

J. Heuer, et al. "Retrovirus-Mediated Gene Transfer of B7-1 and MHC Class II Converts a Poorly Immunogenic Neurblastoma into a Highly Immunogenic One", Mary Ann Liebert, Inc., Larchmont, NY, *Human Gene Therapy*, 7: 2059-2068 (1996).

A. Huang, et al. "Role of Bone Marrow-Derived Cells in Presenting MHC Class I-Restricted Tumor Antigens", American Association for the Advancement of Science, Washington, DC, *Science*, 264: 961-965 (1994).

E. Katsanis, et al. "Irradiation of singly and doubly transduced murine neuroblastoma cells expressing B7-1 and producing interferon-gamma reduces their capacity to induce systemic immunity", Nature Publishing Group, New York, NY, *Cancer Gene Therapy* 3: 75-82 (1996).

E. Katsanis, et al. "B7-1 Expression decreases tumorigenicity and induces partial systemic immunity to murine neuroblastoma deficient in major histocompatibility complex and costimulatory molecules", Nature Publishing Group, New York, NY, *Cancer Gene Therapy*, 2: 39-46 (1995).

Y. Li, et al. "Costimulation by CD48 and B7-1 Induces Immunity against Poorly Immunogenic Tumors", The Rockefeller Univeristy Press, New York, NY, *Journal of Experimental Medicine*, 183: 639-644 (1996).

S. Miyatake, et al. "Defective herpes simlex virus vectors expressing thymidine kinase for the treatment of malignant glioma", Nature Publishing Group, New York, NY, *Cancer Gene Therapy*, 4: 222-228 (1997).

P. Mroz, et al. "Retrovirally Transduced *Escherichia coli gpt* Genes Combine Selectability with Chemosensitivity Capable of Mediating Tumor Eradication", Mary Ann Liebert, Inc., Larchmont, NY, *Cancer Gene Therapy*, 4: 589-595 (1993).

D. Mueller, et al. "Clonal Expansion Versus Functional Clonal Inactivation: A Costimulatory Signalling Pathway Determines the Outcome of T Cell Antigen Occupancy", Annual Reviews, Inc., Palo Alto, CA, *Annual Review of Immunology*, 7:445-480 (1989).

I. Parney, et al. "Granulocyte-Macrophage Colony-Stimulating Factor and B7-2 Combination Immunogene Therapy in an Allogeneic Hu-PBL-SCID/Beige Mouse-Human Glioblastoma Multiforme Model", Mary Ann Liebert, Inc., Larchmont, NY, *Human Gene Therapy*, 8: 1073-1085 (1997).

J. Rao, et al. "IL-12 Is an Effective Adjuvant to Recombinant Vaccina Virus-Based Tumor Vaccines", The American Association of Immunologists, Bethesda, MD, *The Journal of Immunology*, 156: 3357-3365 (1996).

R. Schwartz, et al. "T Cell Anergy", Scientific American, Inc., New York, NY, *Scientific American*, 62-71 (1993).

M. Toda, et al. "In Situ Cancer Vaccination: An IL-12 Defective Vector/Replication-Competent Herpes Simplex Virus Combination Induces Local and Systemic Antitumor Activity", The American Association of Immunologists, Bethesda, MD, *The Journal of Immunology*, 160: 4457-4464 (1996).

L. Zitvogel, et al. "Interlukin-12 and B7.1 co-stimulation cooperate in the induction of effective antitumor immunity and therapy of established tumors", VCH Verlagsgesellschaft mbH, Weinheim Germany, *European Journal of Immunology*, 26:1335-1341 (1996).

WJR Hirst, et al. "Enhanced immune costimulatory activity of primary acute myeloid leukaemia blasts after retrovirus- mediated gene transfer of B7.1", Stockton Press, Basingstoke, UK, *Gene Therapy*, 4: 691-699 (1997).

W. Marti, et al. "Nonreplicating Recombinant Vaccina Encoding Human B-7 Molecules Elicits Effective Costimulation of Naïve and Memory CD4$^+$T Lyumphocytes in Vitro", Academic Press, San Diego, CA, *Cellular Immunology*, 179: 146-152 (1997).

K. Sturmhoefel, et al. "Potent Activity of Soluble B7-IgG Fusion Porteins in Therapy of Established Tumors and as Vaccine Adjuvant", American Association for Cancer Research, Philadelphia, PA, *Cancer Research*, 59: 4964-4972 (1999).

H. Swiniarski, et al. "Immune Response Ehancement by *in Vivo*Administration of B7.21g, a Soluble Costimulatory Protein", Academic Press, San Diego, CA, *Clinical Immunology*, 92: 235-245 (1999).

M. Moro, et al. "Induction of Therapeutic T-Cell Immunity by Tumor Targeting with Soluble Recombinant B7-Immunoglobulin Costimulatory Molecules", American Association for Cancer Research. Philadelphia, PA, *Cancer Research*, 59: 2650-2656 (1999).

P. Challita-Eid, et al. "A B7.1-Antibody Fusion Protein Retains Antibody Specificity and Ability to Activate Via the T Cell Costimulatory Pathway", The American Association of Immunologists, Bethesda, MD, *Journal of Immunology*, 160: 3419-3426 (1998).

R. Cristiano, et al. "Targeted Non-Viral Gene Delivery for Cancer Gene Therapy", Frontiers in Bioscience, Manhasset, NY, *Frontiers in BioScience*, 3: 1161-1170 (1998).

Katsanis, et al., B7-1 Expression decreases tumorigenicity and induces partial systemic immunity . . . , Cancer Gene Ther., 2:39-46, (1995).

Katsanis et al, Irradiation of singly and doubly transduced murine neuroblastoma . . . , Cancer Gene Ther.3:75-82, (1996).

Heuer et al.; Hum.Retrovirus-Mediated Gene Transfer of B7-1 and MHC Class II . . . , Gene Ther., 7:2059-2068, (1996).

Kanner et al., CD2/LFA-3 Ligation induces phospholipase . . . , J. Immunol., 148:2023-9, No. 7, (1992).

Kato et al., CD48 is a counter-receptor for Mouse CD2 and is involved in T Cell Activation, J. Exp. Med., 176:1241-9, (1992).

Hurtado et al., Potential Role of 4-1BB in T Cell Activation . . . , J. Immunol., 155:3360-7, (1995).

Noelle et al., A 39-kDa protein on activated helper T cells binds CD40 and . . . Proc. Natl. Acad. Sci. USA, 89:6550-6554, (1992).

Todo et al., In Situ Expression of Soluble B7-1 in the Context of Oncolytic Herpes Simplex . . . Cancer Res., 61:, 153-161, (2001).

Fry et al., Gene therapy: potential applications in clinical transplantation, Expert Reviews in molecular medicine, 1-24, ISSN 1462-3994 Cambridge University Press, 1462-3994 (1999).

Roth et al., Gene Therapy for Cancer: What have we done and where are we going?, J. National Cancer institute, vol. 89, No. 1, 21-39, (1997).

Ye et al., Gene Therapy for Cancer using single-chain Fv fragments specific for 4-1BB, J. Nature Medicine , vol. 8, 343-348, (2002).

Kooby et al., Oncolytic viral therapy for human colorectal cancer and liver metastases using a multi-mutated herpes simplex virus type-1 (G207), The FASEB Journal, vol. 13, Aug. 1999, pp. 1325-1334.

Walker et al., "Local and Systemic Therapy of Human Prostate Adenocarcinoma with Conditionally Replicating Herpes Simplex Virus Vector G207," Human Gene Therapy, vol. 10, Sep. 1, 1999, pp. 2237-2243.

Oyama et al., "Intravestical and Intravenous Therapy of Human Bladder Cancer by the Herpes Vector G207," Human Gene Therapy, vol. 11, Aug. 10, 2000, pp. 1683-1693.

Carew et al., Selective Infection and Cytolysis of Human Head and Neck Squamous Cell Carcinoma with Sparing of Normal Mucosa by a Cytotoxic Herpes Simplex Virus Type 1 (G207), Human Gene Therapy, , vol. 10, Jul. 1, 1999, pp. 1599-1606.

Delman et al., Effects of Preexisting Immunity on the Response to Herpes Simplex-Based Oncolytic Viral Therapy, Human Gene Therapy, vol. 11, Dec. 10, 2000, pp. 2465-2472.

Bennett et al., "Antitumor efficacy of regional oncolytic viral therapy for peritoneally disseminated cancer," J. Mol. Med, vol. 78, 2000, pp. 166-174.

Cozzi et al., "Intravesical oncolytic therapy using attenuated, replication-competent, herpes simplex viruses G207 and Nv1020 is effective in the treatment of bladder cancer in an orthotopic syngeneic model," The FASEB Journal, express article 10.1096/fj. 00-0533 fje, published on line Mar. 5, 2001.

Ebright et al., "Replication-competent herpes virus NV1020 as direct treatment of pleural cancer in a rat model," The Journal of Thoracic and Cardiovascular Surgery, vol. 1124, 2002, No. 1.

Fields et al, B7.1 is a Quantitatively Stronger Costimulus Than B7.2 in the Activation of Naïve CD8+TCR- Transgenic T Cells, The American Association Immunologists, 1998, pp. 161: 5269-5275.

Kwon et al., Elimination of Residual Metastatic Prostate Cancer After Surgery and Adjunctive Cytotoxic T Lymphocyte-associated Antigen 4 (CTLA-4) Blockade Immunotherapy, PNAS, Dec. 21, 1999, pp. 15074-15079, vol. 96, No. 26.

Henry et al., Structure and Evolution of the Extended B7 Family, Review Immunology Todaym, Jun. 1999, pp. 285-288, vol. 20, No. 6.

* cited by examiner

Figure 1. Construct of amplicon plasmid containing B7-1-Ig gene.

Figure 2. Effect of dvB7-GPT on subcutaneous Neuro2a tumor growth in A/J mice.

Figure 3. Effect of dvB7-GPT on survival of A/J mice with intracerebral Neuro2a tumors.

Figure 4. Lack of effect of dvB7-GPT on subcutaneous Neuro2a tumor growth in nude mice.

USE OF SOLUBLE COSTIMULATORY FACTOR FOR TUMOR IMMUNO-GENE THERAPY

This application claims benefit of priority to provisional U.S. application 60/157,787, filed on Oct. 5, 1999.

The invention was made with government support under grant number NS 32677 awarded by the National Institutes of Health. Accordingly, the U.S. Government has certain rights in this invention.

BACKGROUND OF THE INVENTION

1. Field of the Invention

This invention relates to a gene therapy for neoplasm, wherein a tumor cell is trasnduced with a gene encoding a soluble costimulatory factor. The transduced tumor cell secretes the costimulatory factor which induces T-cells to attack both transduced and untransduced cells of the tumor.

2. Description of the Related Art

The induction of an antigen-specific immune response requires three distinct interactions between antigen presenting cells (APCs) and antigen. The first interaction is adhesion, where APCs and T-cells randomly interact by adhesion molecules, which are cell surface ligands and their respective receptors. The second interaction, recognition, will occur if the APCs can process, transport, and present sufficient quantities of the antigen within a major histocompatibility complex (MHC) molecule. The antigen-MHC is then recognized by the T-cell via the ligation (i.e., binding and cross-linking) of the T-cell receptor complex (TCR) to the antigen-MHC. The third interaction, costimulation, is needed for T-cells to induce cellular proliferation, cytokine secretion, and effector function. The second and third interactions are respectively known as signal 1 and signal 2. If signal 2 is not delivered, T-cells enter anergy, a state of long-term unresponsiveness to specific antigens.

Induction of tumor-specific cytotoxic T lymphocytes (CTL) requires the two signals noted above to be present on APCs. The first signal is a tumor antigen, which is processed, transported to, and presented by MHC class I and/or class II molecules on the surface of APCs. The second signal is a costimulatory molecule present on tumor cells and/or other APCs (Mueller et al., 1989, Annu. Rev. Immunol. 7:445–480). Anergy or tolerance to tumor cells occurs as a result of CD8$^+$ T-cells receiving the signal of a MHC-bound tumor antigen, but not a second signal of costimulatory molecules (Schwartz, 1993, Sci. Am. 269:48–54).

Membrane proteins of the B7 family are known to be the most potent of the costimulatory molecules (Galea-Lauri et al., 1996, Cancer Gene Ther. 3:202–213). However, the expression of a single costimulatory factor on the tumor cell membrane is ineffective in nonimmunogenic tumors, presumably due to the lack of coexpression of MHC-bound tumor antigen (Chen et al., 1994, J. Exp. Med. 179:523–532).

The environment where an immune response is initiated can influence which types of cells become antigen presenting cells. In the peripheral blood, for example, dendritic cell, activated B cells, and monocytes serve as antigen presenting cells, whereas in the skin, keratinocytes and Langerhans cells present antigens. "Professional" APCs are cells such as dendritic cells, activated B cells, and activated macrophages, which can process and present antigens on their surface. Professional APCs have been found to have the ability to present tumor antigens in association with an MHC molecule. Tumor cells also can serve as APCs.

Huang et al. (1994, Science, 264:961–965) have found that MHC class I-restricted tumor antigens usually are not presented by the tumor itself, but by dendritic cells or bone-marrow-derived APCs. Dendritic cells are capable of efficiently presenting antigen derived from apoptotic cells or virus-infected cells, stimulating class I-restricted CD8$^+$ CTLs (Albert et al., 1998, Nature, 392:86–89). Dendritic cells that infiltrate tumors, however, can lack B7 molecules and therefore have reduced T-cell stimulatory activity (Chaux et al., 1996, Lab. Invest., 74:975–983).

Current gene therapies aimed at the control of cancer often fail because none of the current gene vectors are capable of infecting 100% of the cells of a tumor. Consequently, these therapies do not result in total destruction of the tumor.

SUMMARY OF THE INVENTION

The present invention addresses the problem of incomplete tumor antigen immunization by providing a gene therapy that entails delivering, to tumor cells, an expressible nucleotide sequence encoding a soluble costimulatory factor, thereby activating or enhancing the response of T-cells to a tumor. An "expressible nucleotide sequence" is a naturally occurring or man-made nucleotide sequence required for the production of a functional polypeptide.

When the soluble costimulatory factor is expressed within the tumor or the immediate area of the tumor, anergy is overcome, T-cell activation is stimulated, and activated T-cells infiltrating or surrounding the tumor mount an immune response to the tumor cells. Thus, the secreted costimulatory factor induces destruction of tumor cells regardless of whether they have or have not been transformed with the expressible nucleotide sequence.

DETAILED DESCRIPTION OF THE PREFERRED EMBODIMENT

By the use of soluble costimulatory factors, preferably of the B7 family, such as B7-1, the present invention overcomes the problem of T-cell anergy towards poorly immunogenic or nonimmunnogenic tumors. It is desirable to use soluble costimulatory factors such as B7-1 due to the limited ability of tumor cells to function effectively as APCs.

The present invention, by enabling the expression of a soluble costimulatory factor in the tumor environment, allows for T-cells to be activated in at least two ways. First, the presence of the soluble costimulatory factor provides dendritic cells and other APCs surrounding or infiltrating the tumor increased T-cell stimulation. Second, the presence of soluble costimulatory factors in the tumor environment can assist tumor cells in functioning as APCs because most types of tumor cells do not express B7 molecules (Chen et al., 1994, J. Exp. Med., 179: 523–532; Denfeld et al., 1995, Int.

J. Cancer, 62:259–265). The first method of activation alone may suffice in inducing an immune response. Therefore, the second method of activation, antigen presentation by tumor cells themselves, may not be necessary. In addition, the presence of costimulatory factors may reverse the anergic state of primed T-cells to an activated state.

In a preferred embodiment, the soluble costimulator is designed so that two extracellular domains are linked together. It has been shown that cross-linking of neighboring CD28, a counterreceptor on T-cells for the B7 molecule, is essential for T-cell activation (Schwartz et al., 1993, Sci Am, 269:48–54). Hence, a dimeric soluble costimulatory factor should advantageously provide stronger stimulation to T-cells than monomeric factor normally expressed on the cell surface. A preferred linker for the extracellular domains is the Fc portion of immunoglobulin (Ig)G. A particularly preferred embodiment of the soluble costimulatory factor is B7-1-IgG.

The invention is further described by reference to the examples below, with are set forth by illustration only. Nothing therein should be taken as a limitation upon the overall scope of the invention.

EXAMPLE 1

Herpes Simplex Virus Vector Construction

Figure 1:
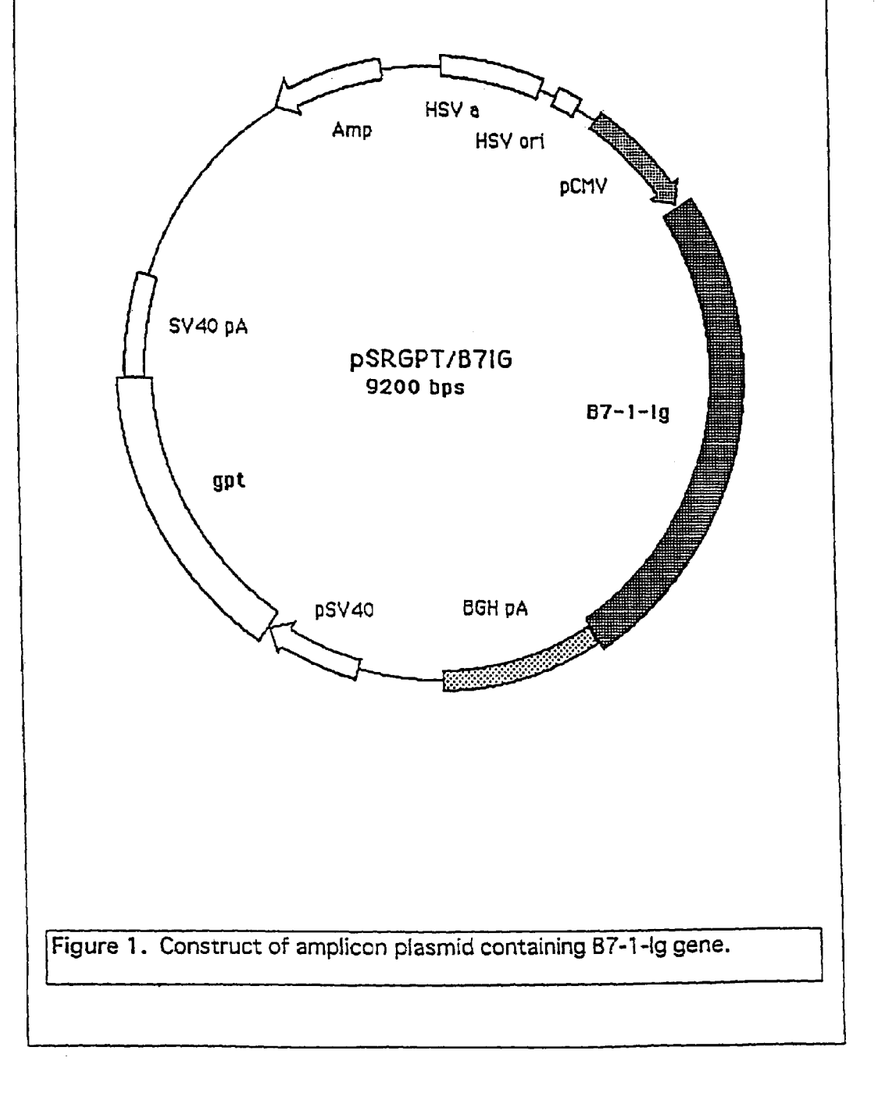
FIG. 1 is a schematic representation of an amplicon plasmid containing a B7-1-Ig gene.

Defective herpes simplex virus (HSV) vectors containing a soluble B7-1 gene were used to demonstate the effectiveness of soluble costimulatory factor in tumor immuno-gene therapy. The soluble B7-1 (B7-1-Ig) was designed as a fusion protein of the extracellular domain of murine B7-1 and the Fc portion of human IgG1. To generate defective HSV vectors, an amplicon plasmid containing the B7-1-Ig gene was designed and constructed (FIG. 1).

The B7-1-Ig gene was initially cut out from the plasmid B7.1-pIg. The gene was inserted into another plasmid (pCR3) so that it is driven by the cytomegalovirus (CMV) immediate early promoter. The entire cassette, including the B7-1-Ig gene, was then cut out to construct the amplicon. The amplicon also contains the *Escherichia coli* gpt gene encoding the enzyme xanthine/guanine phosphoribosyltransferase and is driven by the SV40 promoter.

The gpt gene is used to select for a defective HSV. In the presence of mycophenolic acid with xanthine and hypoxanthine, the replication of helper HSV is blocked, whereas the defective HSV expressing the gpt gene shows a resistance to mycophenolic acid. This results in a defective HSV yield with a high defective to helper ratio. This is a novel approach to the generation of defective HSV vectors that is derived from studies on vaccinia virus vectors (Falkner et al., 1988, J. Virol., 62:1849–1854; Falkner et al., 1990, J. Virol. 64:3108–3111). An added benefit of this vector is that gpt is able to convert the non-toxic substrate 6-thioxanthine (6-TX) into the toxic metabolite 6-TX-triphosphate (Mroz et al., 1993, Hum. Gene Ther. 4:589–595).

The defective HSV vector was generated using multimutated, conditionally-replicating HSV vector G207 as a helper virus and the mycophenolic acid/xanthine/hypoxanthine growth regimen. The defective HSV vector (dvB7-GPT) stock used in the studies had a defective to helper ratio of about 1:40, based on immunohistochemical detection of murine B7-1. A defective HSV vector containing the alkaline phosphatase gene instead of B7-1-Ig gene (dvAP-GPt) was also generated as a control.

EXAMPLE 2

In Vitro Expression of a Soluble Costimulatory Factor

Expression of B7-1-Ig in cultured cells infected by dvB7-GPT was detected by several methods. When Vero (African green monkey kidney) cells and Neuro2a (murine neuroblastoma) cells were infected with dvB7-GPT at a multiplicity of infection (MOI) of 0.25 and 3 (helper titer), respectively, immunohistochemical expression of B7-1-Ig was detected by antibodies against murine B7-1 and human IgG (Fc). When assessed by enzyme-linked immunosorbent assay (ELISA) for human IgG, conditioned medium collected from dvB7-GPT-infected Neuro2a cells (MOI=3) 68 hours post-infection was found to contain 0.34 ng/ml of secreted B7-1-Ig.

EXAMPLE 3

In Vivo Effects of a Soluble Costimulatory Factor

Figure 2:
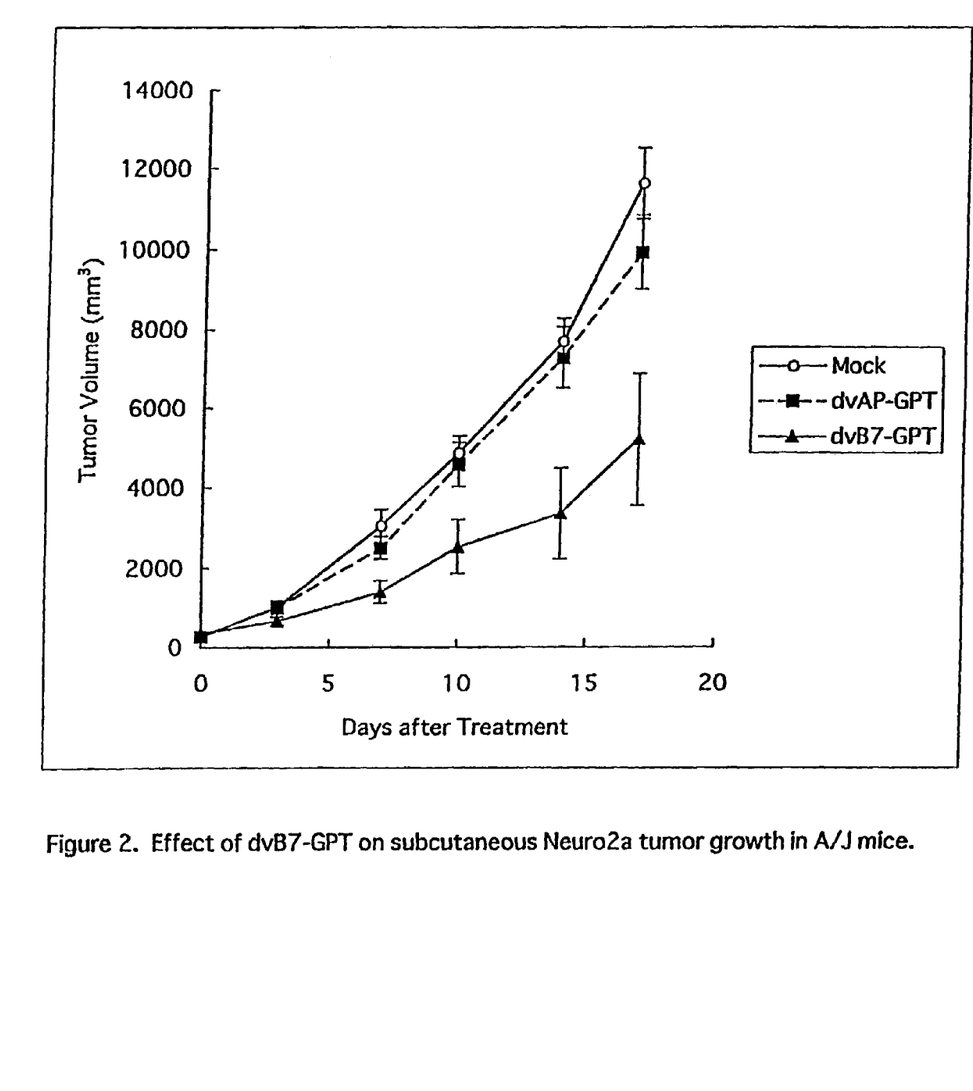
FIG. 2 is a graphic representation of the effect of dvB7-GPT on subcutaneous Neuro2a tumor growth in A/J mice.
Figure 3:
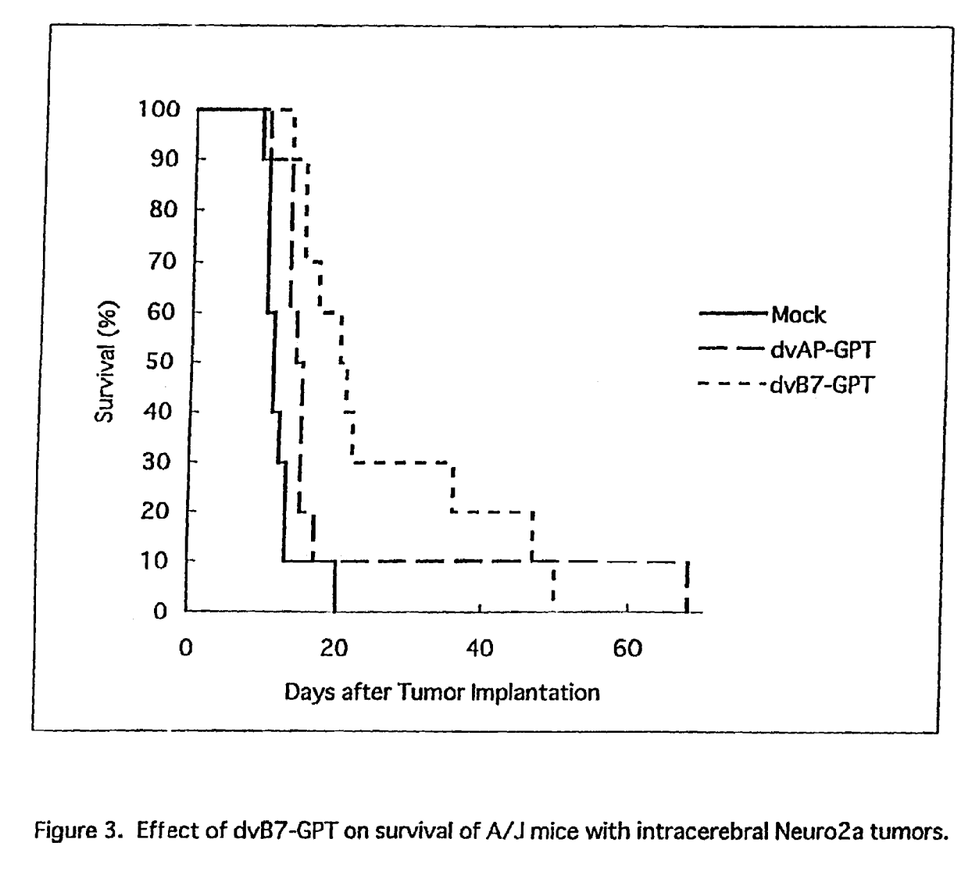
FIG. 3 is a graphic representation of the effect of dvB7-GPT on the survival of A/J mice with intracerebral Neuro2a tumors.

An immunocompetent tumor model of A/J mice and syngeneic Neuro2a cells was used for in vivo studies. When A/J mice harboring established subcutaneous (s.c.) Neuro2a tumors (approximately 6 mm in diameter) were treated with two intratumoral inoculations of dvB7-GPT ($2 \times 10^5$ plaque forming units (pfu) of helper virus). Inoculations were performed three days apart. A significant inhibition of tumor growth was observed compared with mock-infected extract (mock) or dvAP-GPT of the same dose ($p<0.01$ versus mock and $p<0.05$ versus dvAP-GPT at day 17, unpaired t test; FIG. 2). A/J mice were injected intracerebrally with Neuro2a cells and treated five days later with a stereotactic inoculation of dvB7-GPT ($6 \times 10^5$ pfu of helper virus) at the same coordinates. A significant prolongation of median survival was observed compared with mock or dvAP-GPT ($p<0.001$ versus mock and $p<0.05$ versus dvAP-GPT, Wilcoxon test; FIG. 3).

Expression of B7-1-Ig in vivo was detected subcutaneously. Neuro2a tumors were harvested 2 days after dvB7-GPT inoculation and immunostained for human IgG (Fc). When the same tumors were immunostained for CD4, CD8 and Mac-3, abundant $CD4^+$ T-cells and fewer $CD8^+$ T-cells were observed in areas corresponding to dvB7-GPT infection, but were not observed in dvAP-GPT-inoculated s.c. tumors. Mac-3-positive macrophages were observed ubiquitously in both dvB7-GPT- and dvAP-GPT-inoculated tumors.

Figure 4:
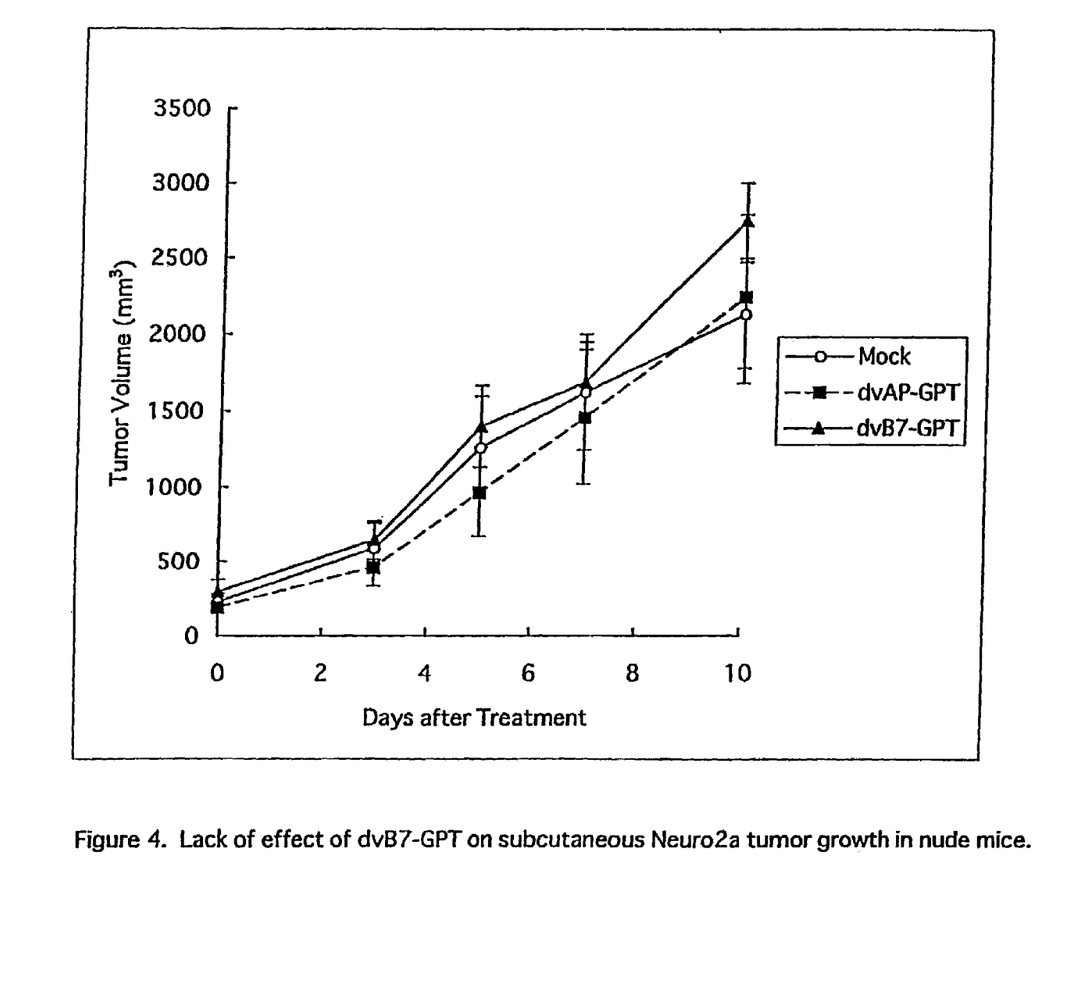
FIG. 4 is a graphic representation of the lack of effect of dvB7-GPT on subcutaneous Neuro2a tumor growth in nude mice.

When athymic nude mice (Balb/c nu/nu) harboring established s.c. Neuro2a tumors (approximately 6 mm in diameter) were treated with intratumoral inoculation of dvB7-GPT in exactly the same manner and dosage as were A/J mice, no significant effect on tumor growth was observed compared with mock or dvAP-GPT (FIG. 4). Thus, B7-1-Ig gene delivery into tumors results in efficient antitumor activity in immunocompetent animals, and the data support that the effect is mediated by a T-cell response.

Survivors from the subcutaneous Neuro2a rechallenge study were further challenged with a subcutaneous injection of SaI/N, A/J-derived sarcoma cells ($5 \times 10^6$). All mice cured by B7-1-Ig, as well as all 6 naïve A/J mice used as controls, showed tumor formation at 4 weeks post-implantation. This finding indicates that the protective antitumor immunity was specific to Neuro 2a cells.

Localized delivery of vectors expressing soluble costimulatory factor are superior to systemic delivery of soluble costimulatory factor due to the following reasons: (1) Local secretion offers an abundant amount of costimulatory factor to APCs that have processed tumor antigens in the tumor-surrounding environment, causing increased T-cell stimulatory activity with a specific direction to the tumor cells. (2) Soluble costimulatory factor secreted from tumor cells should activate local T-cells by reversing the anergic state. (3) Local vector administration causes soluble B7-1 to be expressed almost exclusively by tumor cells, therefore allowing tumors cells, but not other non-professional APCs, to function as APCs. (4) Local vector administration can provide higher concentration and more localized distribution of soluble costimulatory in the tumor and the surrounding region than systemic administration. (5) Systemic administration of soluble costimulatory factor may cause activation of T-cells primed to various types of antigens. Such a non-specific immune response may trigger immune responses against irrelevant antigens, or normal tissues or organs, potentially causing an undesirable toxicity or an autoimmune disease. Vector-mediated local administration of IL-12 has been shown to cause minimal side effects, whereas systemic administration of IL-12 has been found to be relatively toxic in humans.

This invention also can be applied to tumor vaccination using ex vivo methods. Tumor cells surgically obtained from a patient can be grown in culture, transduced with soluble costimulatory molecule gene, and injected subcutaneously into the same patient for tumor vaccination.

The concept of using a soluble costimulatory factor is not limited to B7-1. Rather, other costimulatory factors that are normally expressed on the cell surface of APCs, such as B7-2, CD40, CD72, CD2, can be used. Other costimulatory factors which may be used include B7-3, CD40 ligand, CD70, CD24, LFA-3, CD48, 4-1BB, 4-1BB ligand, LIGHT, ICAM-1 (CD54).

Additionally, different costimulatory pathways work synergistically. Therefore, a combination of two or more different types of costimulatory molecules listed above (soluble or not) is more potent in stimulating the immune response than each costimulatory factor alone, for example, B7-1 and CD48 (Li et al., 1996, J. Exp. Med., 183:639–44). Furthermore, it has been demonstrated in vivo that IL-12 (Rao et al., 1996, J. Immunol., 156:3357–3365; Zitvogel et al., 1996, Eur. Immunol., 26:1335–1341), interferon gamma (Katsanis et al., 1996, Cancer Gene Ther. 3:75–82), GM-CSF (Parney et al., 1997, Hum. Gene Ther., 8: 1073–1085), ICAM-1 (Cavallo et al., 1995, Eur. J. Immunol., 25:1154–1162), or MHC class II (Baskar et al., 1996, J. Immunol. 156:3821–3827; Heuer et al., 1996, Hum. Gene Ther. 7:2059–2068) expressed together with B7 molecules enhances the stimulation of antitumor immunity.

Moreover, the fusion does not have to involve IgG. Rather, any protein or peptide sequence that will allow two B7-1 molecules to cross-link their cognate receptors can be used. Vectors other than the HSV vector described above can be used. These include viral vectors such as herpes simplex virus, retrovirus, adenovirus, adeno-associated virus, vaccinia virus, avipox virus, baculovirus, and reovirus, and others.

Furthermore, other HSV vectors which can be employed include replication-competent HSV, replication-incompetent HSV, and HSV amplicon vectors with or without helper virus. Non-viral vectors as well as viral vectors can potentially be used. The immuno-gene therapy of the present invention can be applied to any type of solid tumor. Delivery can be by direct intratumoral inoculation or systemic delivery.

The neuroblastoma model described herein is predictive of efficacy with other tumor types. It has been previously shown that defective HSV vectors (HSV amplicon vectors with helper HSV) expressing HSV-thymidine kinase or IL-12 can exhibit antitumor effects as effectively as other vectors (retrovirus, adenovirus) with the same transgenes (Miyatake et al., 1997, Cancer Gene Ther. 4:222–228; Toda et al., 1998, J. Immunol. 160:4457–4464). The animal tumor model used to show the effect of soluble B7-1 was chosen because Neuro2a cells form intracerebral tumors as well as subcutaneous tumors reproducibly in A/J mice with a 100% take rate, the tumors are fast-growing, and the model has been used to study the effect of cell surface B7 molecules.

It has been shown that Neuro2a cells transduced with B7-1 alone, even with 100% of cells expressing B7-1, fails to induce significant immunological protection (Heuer et al., 1996, Hum. Gene Ther. 7:2059–2068; Katsanis et al., 1995, Cancer Gene Ther. 2:39–46), which is in agreement with other poorly immunogenic tumors (Li et al., 1996, J. Exp. Med., 183:639–44; Chen et al., 1994, J. Exp. Med. 179: 523–532). Neuro2a is known as one of the most poorly immunogenic cell lines, and therefore, can be considered as one of the most difficult targets for immunogene therapy. Since the present invention is effective with the relatively non-immunogenic Neuro2a cells, one understands that it will be effective with more immunogenic tumors.

We claim:

1. A method of activating or enhancing a T-cell response in a patient with a tumor, comprising administering to said patient, via localized delivery, a pharmaceutical composition comprising a herpes simplex virus vector comprising an expressible nucleotide sequence for a soluble costimulatory factor in the B7 family, which factor is selected from the group consisting of B7-1-Ig and B7-2-Ig, such that (i) said factor is expressed by tumor cells or cells in the immediate area of the tumor, and (ii) said T-cell response thereby is activated or enhanced against said tumor.

2. The method according to claim 1, wherein said administering comprises introducing said composition directly into said tumor or a local area of said tumor.

3. The method according to claim 1, wherein said administering comprises delivering said herpes simplex virus vector into the tumor.

4. The method according to claim 1, wherein said administering comprises injecting said herpes simplex virus vector conjugated to a liposome carrier into the tumor.

5. The method of claim 1, wherein said factor comprises a dimer.

6. The method of claim 5, wherein the monomers of said dimer are connected by a linker.

7. The method according to claim 1, wherein said soluble costimulatory factor is B7-1-Ig.

8. The method according to claim 1, wherein said soluble costimulatory factor is B7-2-Ig.

9. The method of claim 1, wherein said tumor is selected from the group consisting of astrocytoma, oligodendroglioma, meningioma, neurofibroma, glioblastoma, ependymoma, Schwannoma, neurofibrosarcoma, medulloblastoma, germ cell tumor, chordoma, pineal tumor, choroid plexus papilloma, pituitary tumor, and vascular tumor.

10. The method of claim 1, wherein said tumor cells or cells in the immediate area of the tumor are selected from the group consisting of melanoma cells, pancreatic cancer cells, prostate carcinoma cells, head and neck cancer cells, breast cancer cells, lung cancer cells, colon cancer cells, ovarian cancer cells, renal cancer cells, neuroblastomas, squamous cell carcinomas, hepatoma cells, and mesothelioma and epidermoid carcinoma cells.

11. The method of claim 1, wherein said administering further comprises delivering to said patient at least one expressible nucleotide sequence coding for an immune modulator.

12. A pharmaceutical composition comprising (A) a herpes simplex virus vector that contains a gene encoding a soluble costimulatory factor in the B7 family, which factor is selected from the group consisting of B7-1-Ig and B7-2-Ig, and (B) a pharmaceutically compatible carrier.

13. The pharmaceutical composition of claim 12, wherein said herpes simplex virus vector is a defective herpes simplex virus.

14. The pharmaceutical composition of claim 12, wherein said herpes simplex virus vector is a recombinant herpes simplex virus.

15. The pharmaceutical composition of claim 12, wherein said soluble costimulatory factor is B7-1-Ig.

16. The pharmaceutical composition of claim 12, wherein said soluble costimulatory factor is B7-2-Ig.

\* \* \* \* \*